(12) United States Patent
Hewson-Hyde et al.

(10) Patent No.: US 8,192,723 B2
(45) Date of Patent: Jun. 5, 2012

(54) AEROSOL COMPOSITION

(75) Inventors: Claire Louise Hewson-Hyde, Hull (GB); Paul William Robinson, Swanland (GB); Andrea Szeki, Quorn (GB); John McNamara, Hull (GB)

(73) Assignee: Reckitt Benckiser (UK) Limited, Slough, Berkshire (GB)

( * ) Notice: Subject to any disclaimer, the term of this patent is extended or adjusted under 35 U.S.C. 154(b) by 1602 days.

(21) Appl. No.: 11/395,724

(22) Filed: Mar. 31, 2006

(65) Prior Publication Data

US 2007/0231290 A1    Oct. 4, 2007

(51) Int. Cl.
*A61K 9/00*        (2006.01)
(52) U.S. Cl. ......................................... 424/45
(58) Field of Classification Search .............. 424/45
See application file for complete search history.

(56) References Cited

U.S. PATENT DOCUMENTS

| | | | |
|---|---|---|---|
| 3,583,642 A | | 6/1971 | Crowell et al. |
| 4,174,295 A | * | 11/1979 | Bargigia et al. ............... 516/8 |
| 4,324,915 A | | 4/1982 | Roman |
| 4,411,829 A | | 10/1983 | Schulte-Elte et al. |
| 4,434,306 A | | 2/1984 | Kobayashi et al. |
| 5,145,604 A | | 9/1992 | Neumiller |
| 5,935,554 A | | 8/1999 | Tomlinson |
| 6,333,362 B1 | | 12/2001 | Lorant |
| 7,384,572 B2 | * | 6/2008 | Minor et al. ............... 252/67 |
| 2007/0034824 A1 | * | 2/2007 | Felix et al. ............... 252/67 |
| 2007/0098646 A1 | * | 5/2007 | Nappa et al. ............... 424/45 |
| 2007/0108759 A1 | * | 5/2007 | D'Amico ............... 285/116 |
| 2008/0248120 A1 | * | 10/2008 | Anderson et al. ............ 424/489 |

FOREIGN PATENT DOCUMENTS

EP        0793955        9/1997

OTHER PUBLICATIONS

Exxon, 2001 Isopar Product Data Sheet.*
T.W. Graham Solomons, Organic Chemistry, 5th ed., John Wiley & Sons, Inc.: New York, 1992, pp. 52.*

* cited by examiner

*Primary Examiner* — James H. Alstrum-Acevedo
(74) *Attorney, Agent, or Firm* — Norris McLaughlin & Marcus PA

(57) ABSTRACT

A single phase aerosol composition comprising the following constituents:
(a) 5 to 75 wt % of a hydrofluorocarbon(s) (HFC) of vapour pressure greater than or equal to 4 bar at 20° C. (60 psig at 70° F.);
(b) 10 to 30 wt % of a hydrocarbon propellant;
(c) 1 to 70 wt % of a hydrocarbon solvent(s) with a vapour pressure of less than 0.1 mm Hg at 20° C.;
(d) 0.01 to 10 wt % of an active constituent(s) selected from the group which includes fragrances, air-sanitisers, air fresheners, deodorizers, odor eliminators, malodor counteractants, insecticides, insect repellants, medicinal substances, disinfectants, aroma therapy compositions; and,
(e) 0 to 25 wt % of an adjuvant constituent(s) other than (a), (b), (c) or (d).
Methods of making the said composition and aerosol dispensers containing the said composition are also disclosed.

10 Claims, No Drawings

AEROSOL COMPOSITION

The present invention describes a single phase aerosol composition for use in standard liquid gas aerosol cans, a method of manufacture of the composition and aerosol cans comprising the composition.

'Aerosol' is a common industry term to identify a large number of products which are dispensed as a mist, stream, spray, powder or even a foam. Aerosol dispensers are the typical vehicle for the storage of and delivery of personal, household, industrial, and medical products, in an aerosol form which permit for a low cost, easy to use method of dispensing such products. Typically, aerosol dispensers include a container, e.g., a pressurizable canister, which contains a liquid product, such as soap, insecticide, paint, deodorant, disinfectant, air freshener, or the like to be dispensed. A pressurised propellant is also provided to the aerosol dispenser and is used to provide a force sufficient to discharge the liquid product from the container. The user actuates the aerosol dispenser by for example pressing an actuator button in order to dispense the product from the aerosol dispenser.

Optimal product delivery is only achieved by balancing the composition of the product in the pressurised container, the ratio of total propellant to total product and the delivery hardware, typically a valve and an actuator.

The propellant is a key component of the system. The two main types of propellants used in aerosol dispensers today are liquefied gas propellants, such as hydrocarbon (e.g., dimethyl ether, "DME") propellants, hydrofluorocarbon ("HFC") propellants, and compressed gas propellants.

In an aerosol dispenser using liquefied gas-type propellants, the container is loaded with the liquid product and propellant to a pressure approximately equal to, or to a pressure slightly greater than, the vapor pressure of the propellant. Thus filled, the container still has a certain amount of space that is not occupied by liquid. This space is referred to as the "head space" of the aerosol dispenser. Since the container is pressurized to approximately the vapor pressure of the propellant, some of the propellant is dissolved or emulsified in the liquid product. The remainder of the propellant is in the vapor phase and fills the head space. As the product is dispensed, the pressure in the container remains approximately constant as liquid propellant evaporates to replenish discharged vapor. Liquefied gas propellants keep the pressure approximately constant in the aerosol dispenser until the contents are exhausted, thus ensuring a generally consistent spray performance throughout the lifetime of the can. It is common to use a blend of propellant components to achieve best combination of solubility, economics, pressure and safety.

In contrast, to liquefied gas propellants, particularly of the hydrocarbon and hydrofluorocarbon-type propellants, compressed gas propellants (e.g., $CO_2$, $N_2O$, $N_2$) are not in liquid form when packaged in conventional aerosol dispenser; that is, they are present entirely in the vapor phase. Thus, internal vapour pressure of the aerosol dispenser diminishes as the contents are depleted, causing changes in the rate and characteristics of the spray.

The propellant typically used to propel an air freshener liquid product from an aerosol dispenser is a liquefied gas propellant mixture of propane, n-butane and isobutane having a propellant pressure of the region of 40 psig at 70° F. (2.72 atm at 294K). "Propellant pressure" refers to the approximate vapor pressure of the propellant, as opposed to "can pressure," which refers to the gauge pressure contained within the container of a full aerosol device.

Such hydrocarbon propellants, however, undesirably comprise Volatile Organic Compounds ("VOCs"). Broadly defined, "VOC" means any compound of carbon, excluding carbon monoxide, carbon dioxide, carbonic acid, metallic carbides, carbides and ammonium carbonate, which participates in atmospheric photochemical reactions. The content of VOCs in aerosol air fresheners is regulated by various federal and state regulatory agencies, such as the Environmental Protection Agency (EPA) and California Air Resource Board (CARB) according to 55 FR 11418 to exclude only those with negligible photochemical reactivity.

One way to reduce the VOC content in such aerosols is to reduce the amount of the propellant used to dispense the liquid product. However, it has been observed that a reduction in the propellant content adversely affects the product performance if the packaging remains the same. Specifically, reducing the propellant content in an aerosol air freshener resulted one or more of the following, usually undesirably, technical effects:

(a) excessive product retention in the aerosol dispenser (sometimes referred to as "product retention"); namely, after the propellant is depleted, an undesirably large quantity of the product is retained which is undesirable from a consumer standpoint as suggesting premature failure of the aerosol dispenser;

(b) an increase in the size of particles of the dispensed product; undesirable as increased particle size of the aerosolized product frequently resulting in the particles "raining" or "falling out" of the air, minimizing their retention in the air;

(c) a reduction in spray rate, particularly as the container of the aerosol dispenser nears depletion.

Reduction of the particle size can then only be achieved by reconfiguring the hardware of the dispenser, for example by incorporation of a "breakup bar" for inducing turbulence in a product/propellant mixture prior to the mixture being discharged from the spray head, e.g., as disclosed in U.S. Pat. No. 3,583,642.

Alternatively, in order to reduce the VOC content, some current products use formulations comprising solvents such as acetone, which solvent, while not classified as VOCs are very aggressive to surfaces and valve/gadget components and are frequently undesired.

Another method of reducing the VOC content of aerosol compositions is to use a microemulsion. This however suffers from the disadvantages that the formulation is more complex and less economically viable, as well as being more difficult to process. The necessary presence of a surfactant required to form the microemulsion will also present have serious ramifications detracting from product performance, frequently leading to detrimental "fall-out" properties, e.g., see for example EP 0793955 or U.S. Pat. No. 5,145,604.

For a non-emulsion single phase system, the formulation requirements in order to be able to deliver a spray (coarse or fine) make it highly desirable that formulated product is homogeneous, i.e. active ingredients, solvent system, propellant under pressure should form a solution. However, this has been achieved thus far only by the use of very high levels of active ingredient (U.S. Pat. No. 5,935,554).

The desired technical requirements of an aerosol dispenser—low fall out, minimal surface and component damage—as well as spray dryness or wetness, droplet size and rate of spray are determined by propellant concentration and vapor pressure as well as any solvent, if such is present, used in combination with the dispenser and valve hardware. Thus, a technically successful aerosol dispenser requires that many variables be delicately balanced in order to assure good performance of the said dispenser.

It is in this context that the present invention describes an aerosol composition having a reduced VOC content compatible with regulatory requirements, suitable for use in conventional dispensers, and which still possesses advantageous technical performance characteristics, namely one or more, preferably two or more and most desirably each of the following features: (i) single phase; (ii) good spray performance, i.e. low fall out; (iii) minimal level of aggressive solvent components, e.g. acetone deleterious to one or more parts of the aerosol dispenser; (iiii) compliance with current (2006) USA VOC regulations; (v) compliance with certain USA regulatory requirements.

Throughout this specification, components referred to in the singular followed by an "s" in parentheses are to be understood as referring to both a single such component or material, or a plurality of such components or materials.

According to a first aspect of the invention, there is provided a single phase aerosol composition comprising the following constituents:
- (a) 5 to 75 wt % of a hydrofluorocarbon(s) (HFC) of vapour pressure greater than or equal to 4 bar at 20° C. (60 psig at 70° F.);
- (b) 10 to 30 wt % of a hydrocarbon propellant;
- (c) 1 to 70 wt % of a hydrocarbon solvent(s) with a vapour pressure of less than 0.1 mm Hg at 20° C.;
- (d) 0.01 to 10 wt % of an active constituent(s) selected from the group which includes fragrances, air-sanitisers, air fresheners, deodorizers, odor eliminators, malodor counteractants, insecticides, insect repellants, medicinal substances, disinfectants, aroma therapy compositions; and,
- (e) 0 to 25 wt % of an adjuvant constituent(s) other than (a), (b), (c) or (d);

wherein (a), (b), (c), and (e) total 100, it being understood that the amount of the (d) active constituent(s) is in addition to and is based on the total of the amounts of (a), (b), (c) and when present, (e).

The selection of the amounts and nature of components (a), (b) and (c) requires careful consideration of the final properties of the aerosol, i.e. minimised fall-out, and requires balancing economic requirements, e.g. cost and amount of aerosol, with the desired product's performance, e.g. maximising aerosol pressure, and selecting the correct hardware in the aerosol dispenser, particularly in the aerosol actuator device in order to optimise performance, e.g. by variation of key parameters such as bore length and size of exit orifice.

Preferably the (a) HFC constituent is selected from the group which includes fluorocarbons 134a, 152a, 227ea and 236fa or mixtures thereof. More preferably the (a) constituent comprises, but more preferably consists essentially of a fluorethane, especially 1,1-difluorethane (152a).

Preferred is a composition as hereinbefore described which comprises 5 to 40 wt % (a) HFC, more preferably one which comprises 7.5 to 35 wt % of the (a) HFC constituent, especially one which comprises 8 to 32 wt % (a) HFC constituent.

Preferably in the composition as hereinbefore described, the (b) hydrocarbon propellant constituent is selected from the group which includes n-butane, i-butane, propane and DME or a mixture thereof. More preferably the (b) hydrocarbon propellant constituent is a mixture of n-butane, i-butane and propane collectively known by the trade reference "Butane X", wherein "X" is a number referring to the partial pressure of the mixture in psig at 70° F., with especially preferred examples being Butane 31, Butane 46 and Butane 70.

Preferred is a composition as hereinbefore described which comprises 10 to 30 wt % butane, more preferably 20 to 30 wt % butane, especially 25 to 30 wt % butane as the (b) hydrocarbon propellant constituent.

Preferred is a composition as hereinbefore described wherein the (c) hydrocarbon solvent constituent is a synthetic isoparaffinic aliphatic hydrocarbon of vapor pressure less than 0.1 mm Hg at 20° C. and has vapor pressure more than 0.03 mm Hg, especially one which has vapor pressure less than 0.1 mm Hg and more than 0.06 mm Hg.

Preferred is a composition as hereinbefore described wherein the (c) hydrocarbon solvent constituent is a paraffinic distillate of distillation point less than about 275° C. Preferably, the (c) hydrocarbon solvent constituent is a low vapor pressure (LVP) solvent, as defined by the California State Exemption, which exempts LVP-VOCs from the VOC content of over 96 categories of specifically regulated consumer products. This Regulation defines LVP-VOC as a compound or mixture which contains at least one carbon atom and meets one of the following: (a) has a vapor pressure less than 0.1 mm Hg at 20° C. as determined by California Air Resources Board's (ARB) Method 310, section 3.6.3; or (b) is a compound with more than 12 carbon atoms, or a mixture comprised solely of compounds with more than 12 carbon atoms and the vapor pressure is unknown; or (c) is a compound with a boiling point greater than 216° C. as determined by ARB method 310 section 3.6.2; or (d) is the weight percent of a mixture that boils above 216° C. as determined by ARB Method 310, section 3.6.2. For the purposes of this definition, "compound" means a molecule of definite chemical formula and isomeric structure, and "mixture" means a substance comprised of two or more compounds. Especially preferred are the hydrocarbon solvents presently commercially available as Isopar® M to be primarily a mixture of $C_{13}$-$C_{14}$ isoparaffins, Isopar® P to be primarily a mixture of $C_{12}$-$C_{20}$ isoparaffins and Isopar™ V also to be primarily a mixture of $C_{12}$-$C_{20}$ isoparaffins ex., ExxonMobil. Preferred is a composition as hereinbefore described which comprises 5 to 65 wt % of a (c) hydrocarbon solvent constituent, preferably 10 to 65 wt % especially preferably 25 to 65 wt % f a (c) hydrocarbon solvent constituent.

Preferred is a composition as hereinbefore described wherein the (d) active constituent is a fragrance or is otherwise useful as an air freshener.

Preferably, the fragrance or air freshener is a fragrance comprising one or more volatile organic compounds which are available from perfumery suppliers such as Firmenich Inc., Takasago Inc., Noville Inc., Quest Co., International Flavors & Fragrances, and Givaudan-Roure Corp.

A wide variety of chemicals are known for perfumery, such as aldehydes, ketones, esters, alcohols, terpenes, and the like. Most conventional fragrance materials are volatile essential oils. A fragrance can be relatively simple in composition, or can be a complex mixture of natural and synthetic chemical components.

Natural fragrances include naturally derived oils such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like. Natural perfumes include the extracts of blossoms, stems and leaves, fruits, fruit peel, roots, woods, herbs and grasses, needles and branches, resins and balsams. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetivert oil, olibanum oil, galbanum oil, ladanum oil and lavendin oil.

Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams.

Synthetic types of fragrance compositions either alone or in combination with natural oils are described in U.S. Pat. Nos. 4,324,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

It is, however, preferred to use mixtures of different perfume compounds which, together, produce an agreeable fragrance The following are also preferably used either individually or in the form of mixtures: dihydromyrcenol, lilial, lyral, citronellol, phenylethyl alcohol, α-hexylcinnamaldehyde, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, benzyl acetate, rose oxide, romillat, irotyl and floramat.

Preferred is a composition as hereinbefore described which comprises 1 to 5 wt % of an (d) active constituent(s), preferably 2 to 3 wt % and, especially preferably 2 to 2.5 wt % of an (d) active constituent(s).

Although optional, the composition may also comprise up to 25 wt % of an adjuvant constituent(s) known to the relevant art, including but not limited to one or more of: corrosion inhibitors, preservatives, biocides, pH modifiers and buffers, surfactants, oil components, emulsifiers, stabilizers, polymers, silicone compounds, antioxidants, film formers, solubilizers, preservatives, colorants such as pigments or dyes and the like.

In a first preferred embodiment of the first aspect of the invention as hereinbefore described there is provided a composition comprising, but preferably consisting essentially of:
  20 to 40 wt % of (a) HFC(s);
  15 to 30 wt % of (b) hydrocarbon propellant(s);
  20 to 50 wt % of (c) hydrocarbon solvent(s); and
  1 to 5 wt % of (d) active constituent(s)
  wherein the total amount of (a), (b) and (c) are 100% wt.

In a second preferred embodiment of the first aspect of the invention as hereinbefore described there is provided a composition comprising, but preferably consisting essentially of:
  25 to 35 wt % of (a) HFC(s);
  25 to 30 wt % of (b) hydrocarbon propellant(s);
  35 to 45 wt % of (c) hydrocarbon solvent(s); and
  2 to 3 wt % of (d) active constituent(s)
wherein (a), (b) and (c) total 100 % wt.

In a third, particularly preferred embodiment of the first aspect of the invention as hereinbefore described there is provided a composition comprising, but preferably consisting essentially of:
  28 to 32 wt % 1,1-difluoroethane 152a;
  25 to 30 wt % Butane 31;
  38 to 42 wt % hydrocarbon solvent Isopar™ M®; and
  2 to 2.5 wt % fragrance
  wherein (a), (b) and (c) total 100.

According to a second aspect of the invention, there is provided a method of manufacture of a composition hereinbefore described which comprises the steps of:
  A) combining the (d) active ingredient(s) with the (c) hydrocarbon solvent constituent and when present, the (e) adjuvant constituent to form a homogeneous mixture;
  B) transferring the resultant homogenous mixture to the container of an aerosol device;
  C) pressuring the container and said mixture with the (b) hydrocarbon propellant constituent and the (a) HFC constituent;
  D) sealing the container with a valve.

According to a third aspect of the invention, there is provided an aerosol dispenser comprising a composition as hereinbefore described.

Any standard form of commercial aerosol dispenser may be employed to dispense compositions according to the first aspect of the present invention, including but not limited to: aluminum and tin-plated steel containers, optionally comprising coatings and/or internal container linings, for example resin coatings such as epoxy resin resins. Typical volume capacities of the containers may be any useful volume typical for aerosol containers, advantageously are in the range 2 fl oz to 34 fl oz.

The invention will now be further described by the embodiment described below, but this should not be thought of restricting in any way the invention as hereinbefore described.

EXAMPLES

Example 1

The following were combined to form a homogenous mixture
  40 wt % Isopar™ M®; and
  2.25 wt % fragrance.
The resultant mixture was then transferred to a standard tinplate aerosol container of volume 325 ml. The container was subsequently charged with:
  30 wt % HFC 152a; and
  30 wt % Butane 31
and was sealed with an actuator valve.

The resultant aerosol container gave excellent performance throughout the lifetime of the container, as evidenced by "fall out" results on standard oil/fragrance scientific paper, which showed little or no black staining due to the fall out of fragrance components.

Example 2

The method of example 1 was repeated however utilizing the following materials and amounts thereof:
  50 wt % Isopar® M
  2.25 wt % fragrance
The resultant mixture was then transferred to a standard tinplate aerosol container of volume 325 ml. The container was subsequently charged with:
  30 wt % Butane 46
  20 wt % HFC 152a.
and was sealed with an actuator valve.

Example 3

The method of example 1 was repeated however utilizing the following materials and amounts thereof:

60 wt % Isopar® M
2.25 wt % fragrance

The resultant mixture was then transferred to a standard tinplate aerosol container of volume 325 ml. The container was subsequently charged with:

30 wt % Butane 46
10 wt % HFC 152a.

and was sealed with an actuator valve.

The invention claimed is:

1. A single phase aerosol composition consisting essentially of the following constituents:
   (a) 8 to 32 wt % of a hydrofluorocarbon(s) of vapour pressure greater than or equal to 4 bar at 20° C. (60 psig at 70° F.);
   (b) 25 to 30 wt % of a hydrocarbon propellant;
   (c) 25 to 65 wt % of a hydrocarbon solvent(s) with a vapour pressure of less than 0.1 mm Hg at 20° C.;
   (d) 1 to 5 wt % of a fragrance; and,
wherein (a), (b) and (c) total 100, it being understood that the amount of the (d) fragrance is in addition to and is based on the total amounts of (a), (b), and (c).

2. A composition according to claim 1 wherein the (a) hydrofluorocarbon constituent is selected from the group comprising fluorocarbons 134, 152a, 227ea and 236fa or mixtures thereof.

3. A composition according to claim 1 wherein the (a) hydrofluorocarbon constituent is difluorethane (152a).

4. A composition according to claim 1 wherein the (b) hydrocarbon propellant constituent comprises n-butane, i-butane, propane or a mixture thereof.

5. A composition according to claim 1 wherein the (c) hydrocarbon solvent constituent is a paraffinic distillate of distillation point less than about 275° C.

6. A composition according to claim 5 wherein hydrocarbon solvent (c) is selected from the group comprising: synthetic isoparaffinic aliphatic hydrocarbon of vapor pressure less than 0.1 mm Hg at 20° C. and has vapor pressure more than 0.03 mm Hg.

7. A composition according to claim 1 which comprises 25 to 65 wt % of the (c) hydrocarbon solvent constituent.

8. A composition according to claim 1 which comprises 2 to 3 wt % of fragrance (d).

9. A method of manufacture of a composition according to claim 1 which comprises the steps of:
   A) combining fragrance (d) with the hydrocarbon solvent (c) to form a homogeneous mixture;
   B) transferring the resultant homogenous mixture to the container of an aerosol device;
   C) pressuring the container and said mixture with the hydrocarbon propellant constituent (b) and the HFC constituent (a);
   D) sealing the container with a valve.

10. An aerosol dispenser comprising a composition according to claim 1.

* * * * *